United States Patent [19]
Feldman et al.

[11] Patent Number: 5,690,115
[45] Date of Patent: Nov. 25, 1997

[54] DETECTING VASCULAR STENOSIS IN CHRONIC HEMODIALYSIS PATIENTS

[76] Inventors: Charles L. Feldman, 233 Maynard Rd., Framingham, Mass. 01701; Kenneth Kleinman, 4334 Jubilo Dr., Tarzana, Calif. 91356; Thomas Shook, 404 S. Irving Blvd., Los Angeles, Calif. 90020

[21] Appl. No.: 531,940

[22] Filed: Sep. 21, 1995

[51] Int. Cl.$^6$ ............................................. A61B 8/06
[52] U.S. Cl. ............................................. 128/661.08
[58] Field of Search .................... 128/660.05–662.06, 128/691–692

[56] References Cited

U.S. PATENT DOCUMENTS

| | | | |
|---|---|---|---|
| 3,641,994 | 2/1972 | Gosling et al. | 128/691 |
| 4,515,164 | 5/1985 | Slavin | 128/663 |
| 4,665,925 | 5/1987 | Millar | 128/663 |
| 4,757,822 | 7/1988 | DiGiulimaria et al. | 128/663 |
| 4,957,110 | 9/1990 | Vogel et al. | 128/692 X |
| 5,040,422 | 8/1991 | Frankenberger et al. | 128/692 X |
| 5,226,421 | 7/1993 | Frisbie et al. | 128/692 X |
| 5,259,385 | 11/1993 | Miller et al. | 128/662.05 X |
| 5,289,821 | 3/1994 | Swartz | 128/661.09 |
| 5,368,034 | 11/1994 | Isner | 128/691 X |
| 5,453,576 | 9/1995 | Krivitski | 128/661.08 |
| 5,505,204 | 4/1996 | Picot et al. | 128/661.1 |

OTHER PUBLICATIONS

Geschwind, Melnik, Kvasnick, Dupouy, Dynamic Detection of Coronary Stenosis by Doppler–Tipped Guidewire, Abstract in JACC, Feb. 1995.

*Primary Examiner*—Francis Jaworski
*Attorney, Agent, or Firm*—Fish & Richardson P.C.

[57] ABSTRACT

Stenotic regions in the vasculature of chronic hemodialysis patients are detected and monitored by blood velocity measuring.

45 Claims, 2 Drawing Sheets

TYPICAL PROFILE OF VELOCITY IN VEIN & SHUNT DURING 60 SEC PULLBACK

DETECTING VASCULAR STENOSIS IN CHRONIC HEMODIALYSIS PATIENTS

The present invention relates to detecting and monitoring partial occlusions in the vasculature ("stenoses") and, more specifically, measuring the size of the occlusions in the vasculature of chronic hemodialysis patients.

Peripheral and sometimes more central veins in the arm (or at times the leg) of patients with kidney failure who require regular hemodialysis can be "arterialized" by shunting blood directly from an anatomically adjacent artery to the vein, bypassing the normally intervening arteriolar and capillary bed. The creation of this arteriovenous shunt can be performed with either native vessel, heterograft or synthetic materials. This "shunt" enables high flow rates (typically 200 to 500 milliliters per minute) of blood to be removed from the circulation, passed through the dialyzer (artificial kidney) and returned to the venous system of the individual patient.

Due to a combination of blood turbulence, foreign body reaction, response to repeated venipuncture (needle sticks of blood vessels), inflammatory reactions from the dialyzer and other poorly understood complex biochemical phenomena, dialysis patients experience frequent vascular occlusions caused by blood clots which form secondary to high grade stenoses of the vessel wall. The stenoses results from proliferation of vascular smooth muscle and inflammatory cells, and connective tissue stroma. The site of stenosis occurs most commonly in the venous outflow tract often in proximity to the surgical anastomotic site. Occlusion of the graft requires emergency declotting and may often require repair of the vein, bypass of the diseased vessel and frequently replacement of the shunt with a new graft in a new anatomical venous position. Typical shunt life is two years with declotting required even more frequently than graft replacement. Total occlusion causes an emergency situation that often has devastating consequences and may require emergency hemodialysis and temporary catheterization of blood vessels with attendant risks.

In summary, the invention enables detection and monitoring of stenotic regions in the vasculature of chronic hemodialysis patients by employing a blood velocity measuring instrument. It is convenient to refer to blood vessels and other blood-carrying passages as blood conduits.

Other features and advantages will become apparent from the following detailed description and accompanying drawing, in which.

Figure 1:
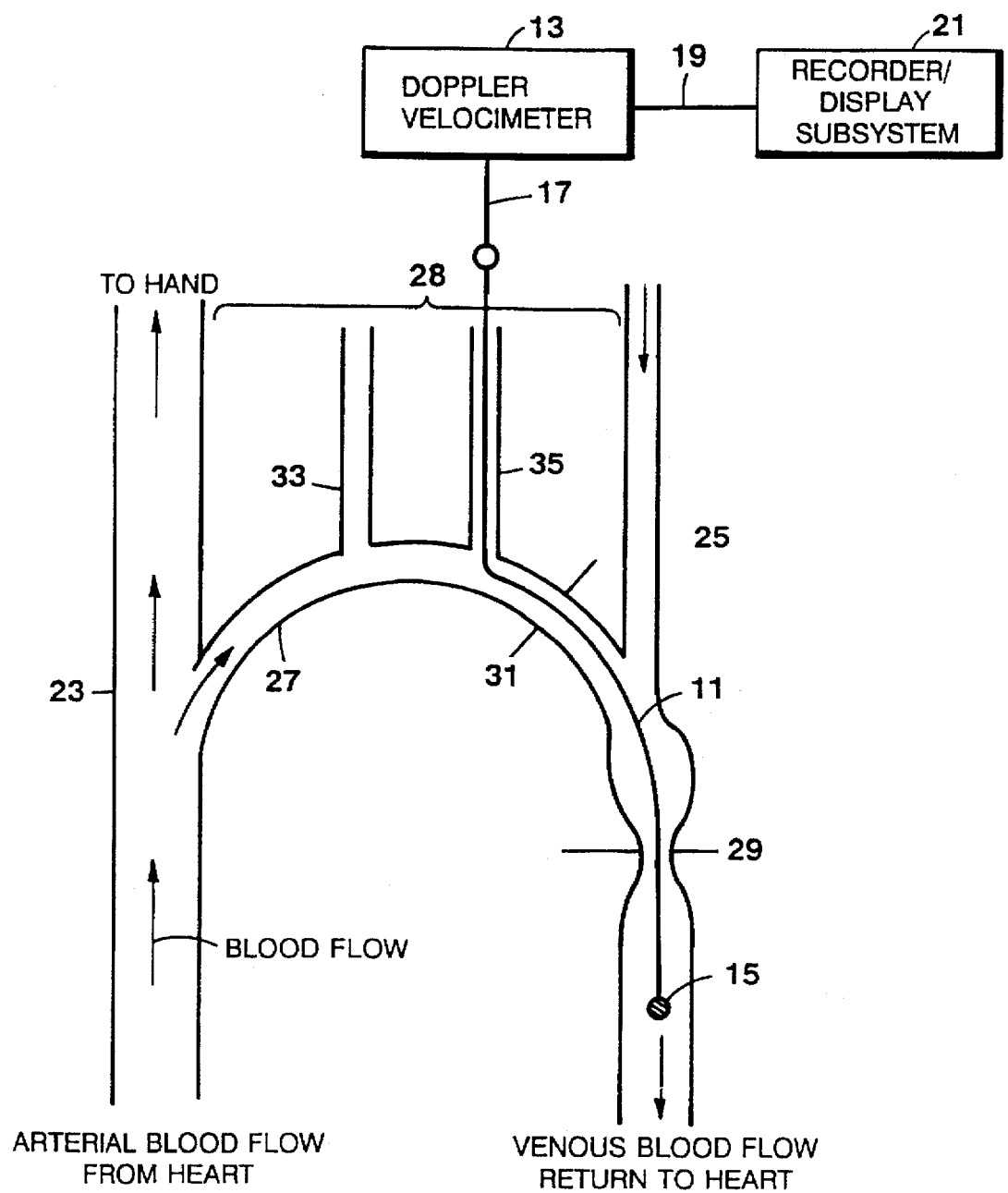
FIG. 1 is a schematic diagram of a system for detecting vascular stenoses.

Referring to FIG. 1, a system 8 for detection and monitoring a stenotic region in the vasculature includes a catheter (or an instrumented guidewire) 11 of a diameter sufficiently small to be inserted into a studied blood vessel and the shunt 28 which has been surgically inserted between the selected vein and artery. Preferably, the catheter or instrumented wire is of sufficiently small diameter to fit through a conventional dialysis needle which is routinely used during dialysis to remove blood, pass it through the dialysis machine and return it to the body. (Alternatively, if a selected vein and artery have been surgically connected to create an artificial fistula (Cimino-Brescia fistula), the catheter (or instrumented wire) must be of sufficiently small diameter to be inserted into the studied vein, preferably through a dialysis needle.) Shunt 28 includes typically a 6 to 12 inches long blood flow conduit 27 that is pierced for dialysis by "arterial" dialysis needle 33, connected to convey blood to a dialyzer, and a "venous" dialysis needle 35, used for return of dialyzed blood to the body. Doppler catheter or wire 11 has at or near its distal end a doppler transducer 15 and its proximal end is coupled to a doppler velocimeter 13 via a cable 17. Doppler velocimeter 13 provides an excitation signal to doppler transducer 15 and decodes the detected doppler signal to determine velocity of the blood flow. The velocity signal is coupled via a cable 19 to a display or a recording device 21. Doppler catheter 11 may have marks that denote a distance from the transducer. A suitable doppler catheter is the Mikro-Tip Model Catheter DC-201, and a suitable doppler velocimeter is the Pulsed Doppler Velocimeter Model MDV-20 both available from Millar Instruments, Inc., Houston, Tex.

The Millar pulsed doppler measuring system operates at a frequency of 20 MHz. The MDV-20 unit provides an excitation signal to the doppler transducer and decodes the detected doppler signal to measure the velocity. The MDV unit has an electrical output proportional to the instantaneous velocity and a corresponding audio output both of which are useful for monitoring quality of the detected signal. An operator can determine whether the blood flow is laminar or turbulent and whether the doppler transducer is positioned against the vessel wall, which yields an unreliable measurement. The MDV-20 unit also has an electrical output proportional to the time-averaged blood flow velocity. The output signal is coupled via cable 19 to a display (for example, a simple oscillographic display) or recording device 21, which may be regarded as a processor for example, a direct writing recorder such as an electrocardiograph or a computer. The computer may be a "subnotebook" computer AMBRA SN866C (made by Ambra Computer Corporation, Raleigh, N.C.) equipped with an analog to digital converter such as Computer Boards DAS08 (made by Computer Boards, Inc. Mansfield, Mass.). The computer uses a data acquisition software, such as Labtech's Notebook (made by Labtech, Inc., Wilmington, Mass.), that stores and displays the velocity data and can send the data to any conventional computer printer, for example, a Canon BJ 200ex (made by Canon Inc. Tokyo, Japan). The storage and display of the data may also be accomplished by other instruments (for example, made by Marquette Electronics Milwaukee, Wis., or Hewlett Packard Andover, Mass.) made for recording physiological data and usually used in a cardiac catheterization laboratory.

The above-described system may also include a mechanized or manual drive unit for withdrawing (or introducing) catheter 11 in a controlled manner at a selectable rate. Alternatively, it may include a flexible distance measuring device (such as the LX series made by Unimeasure of Corvalis, Oreg.) which outputs an electrical signal representative of the length of the catheter currently inserted into the patient.

Doppler system 8 is employed to detect an occlusion in the vasculature of a chronic hemodialysis patient. As shown in the drawing, to accommodate blood flow necessary for dialysis, shunt 28 is often surgically inserted between the selected vein and artery. The shunt can be made of polytetrafluoroethylene (PTFE), a native vessel, bovine graft, or other synthetic material, includes typically blood flow conduit 27 typically 4 mm to 7 mm in diameter and is pierced for dialysis by an "arterial" dialysis needle 33 and a "venous" dialysis needle 35. Preferably, an operator introduces doppler catheter 11, approximately one millimeter in diameter and about 70 to 90 centimeters long, through one of the dialysis needles (most commonly the "venous" needle 35) into the vein 25 either immediately before or immediately following a dialysis session. Alternatively, the procedure can be performed at some time not in conjunction with a dialysis session by introducing the doppler catheter into the graft or the vein to be studied in the same manner as if it were done in conjunction with a dialysis session. The operator passes the tip of catheter 11 to the farthest part of the venous system to be investigated. Then, the operator notes the location of transducer 15 and checks its position relative to the site of insertion into the venous needle of the venous anastomosis. The operator may also check the orientation of the emitter of transducer 15 relative to the blood flow in order to ensure reliable data.

To locate a stenosis, catheter 11 is slowly retracted while the system collects, records and displays the phasic velocity, (i.e., the velocity varying with the heartbeat cycle) and the mean velocity averaged over a few beats. The retraction is done either manually by the operator or automatically by the drive unit. A stenosis in the examined vein or the dialysis shunt is detected from a local, usually rapid, increase in the measured velocity of the blood flow. This significant change in velocity can be observed manually, or the signal can be transduced electronically via a color flow doppler system, computer graph representation, visual or sound metering system to represent the location, and the location of the occlusion determined by observing the length of catheter remaining beyond the dialysis needle entrance. In a narrowed location of the vein, blood has to flow faster to transport the same volume of blood as is transported in a wider location. Alternatively, the system can automatically note the velocity "step-up" and record the location of the corresponding stenosis. The system may also collect information representative of the type of blood flow in the examined vein. Often, near a stenosis the type of blood flow changes from laminar to turbulent with corresponding changes in the phasic velocity. Alternatively, the velocity profile can be collected and stenoses mapped during the initial insertion of catheter 11 to a distal region of the examined vessel.

Figure 2:
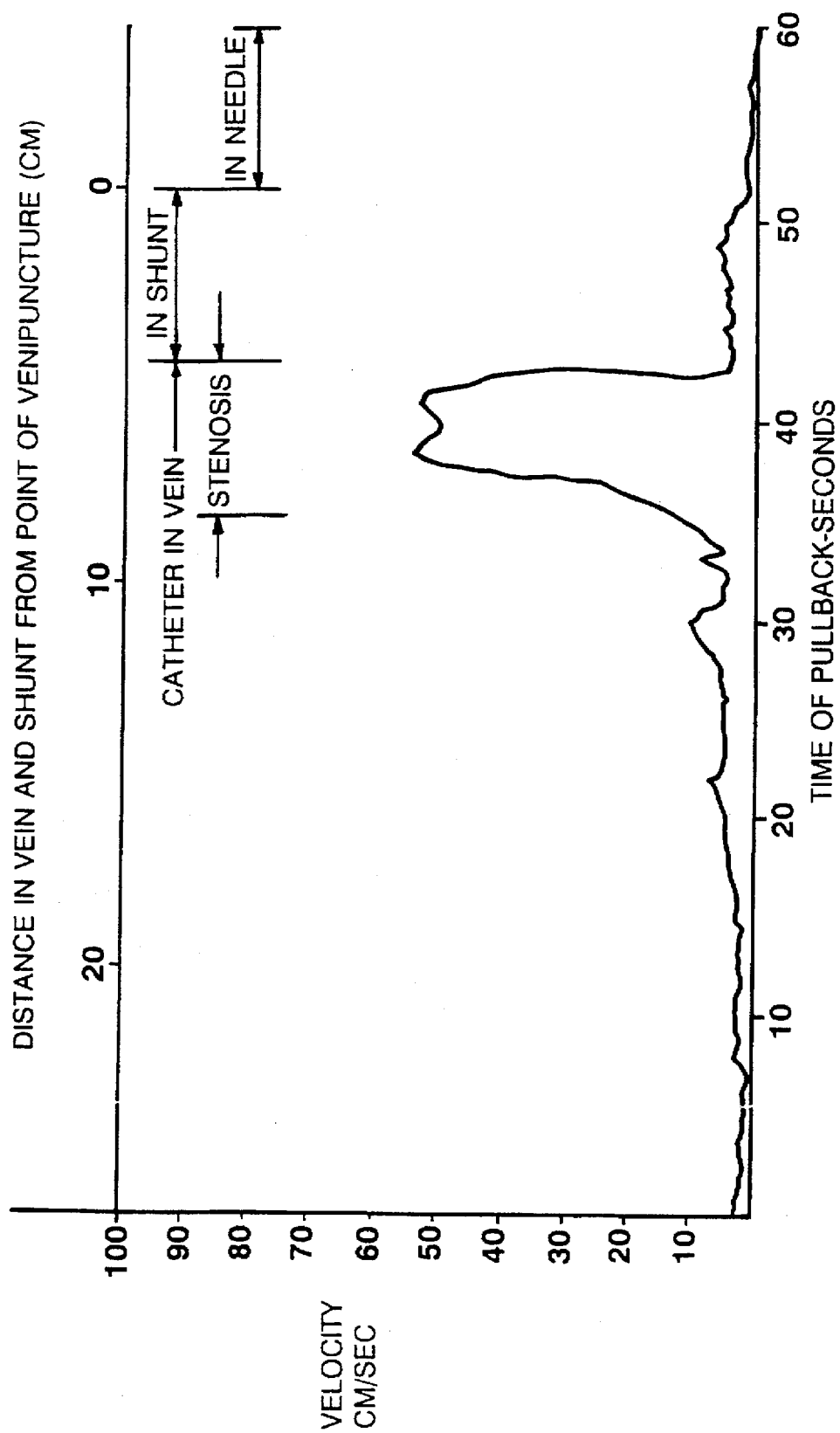
FIG. 2 is a graphical representation of velocity signal as a function of distance from venous cannulation showing a significant change at the location of an occlusion.

Referring to FIG. 2, there is shown a graphical representation of velocity signal as a function of distance from the dialysis needle entrance showing a significant change at distance X. A significant change is typically at least about 2 to 4 times the amplitude at other distances.

In a modification of the above embodiment, the velocity profile along the shunt and/or vein is gathered at separate times. The step-up in velocity at the later time is compared with that at the earlier time. An increase in step-up at the later time would indicate a worsening stenosis.

In another embodiment, the system is further constructed to determine a cross-sectional area of a detected stenotic region 29 of the examined blood vessel. To measure the cross-sectional area, the system measures the blood flow velocity in the examined stenotic region and in a zone of a known cross-sectional area. If substantially all blood that passes through the zone also flows in the examined blood vessel, the cross-sectional area of stenotic region 29 is calculated by the computer from the following equation:

$$A_n = A_k \times (V_k/V_n) \tag{1}$$

where $A_k$ is the known cross-sectional area 31 of the shunt (or another blood flow lumen) and $V_k$ and $V_n$ are the measured blood velocities at narrowed region 29 and zone 31, respectively.

If the cross-sectional area of catheter 11 is significant relative to the measured cross-sectional area, for example, about 10% or more, the cross-sectional area ($A_c$) of catheter 11 should be taken into account. In this case, the cross-sectional area ($A_n$) the stenosis is calculated using the following equation:

$$A_n = A_c + (A_k - A_c) \times (V_k/V_n) \tag{2}$$

wherein $A_c$ is the cross-sectional area of catheter 11, and the other symbols are the same as in equation (1).

A similar procedure can be performed to examine the artery 23. Doppler catheter 11 may be introduced through "arterial" dialysis needle 33 into a distal location of the artery 23 to be investigated. Doppler system 8 can measure the arterial velocity profile to detect a partial occlusion. The cross-sectional area of a detected arterial occlusion can be calculated using Eq. 1. after measuring the blood flow velocity in the occlusion and in a zone 27 having a known cross-sectional area.

In another embodiment, the pulsed doppler velocity measuring system may be replaced by an electromagnetic flowmeter, continuous wave ultrasonic or other types of velocity measuring devices which could be inserted into the patient's vasculature.

An important advantage of the invention is that detection of blood conduit narrowing occurs early enough to allow correction before serious symptoms occur and/or dialysis access failure. For example, angioplasty or elective surgical correction may be used to reduce the partial occlusion before the occurrence of graft clotting and loss of dialysis access and/or physical symptoms or complete occlusion. Other embodiments are within the following claims.

What is claimed is:

1. A method of detecting an occlusion in a blood conduit of a hemodialysis patient comprising:

inserting a velocity detector into an examined blood conduit at a selected site;

measuring velocity of the blood flow in a first region of the examined blood conduit;

moving said velocity detector to a second region of the examined blood conduit;

measuring velocity of the blood flow in at least a second region of the examined blood conduit;

and comparing the velocities measured in the different regions to obtain an indication of an occlusion in said blood conduit.

2. The method of claim 1 wherein said inserting a velocity detector includes positioning said velocity detector into a distal region of the examined blood conduit and said moving said velocity detector include moving said velocity detector to a proximal region relative to said site.

3. The method of claim 1 wherein said inserting step includes introducing into the examined blood conduit a doppler catheter comprising a doppler transducer mounted substantially at its distal end.

4. The method of claim 3 wherein said inserting step includes positioning said doppler transducer at a distal region of the examined blood conduit relative to said site and said moving steps include retracting said doppler catheter.

5. The method of claim 4 wherein said retracting of said doppler catheter is performed at a substantially constant rate.

6. The method of claim 1 wherein said inserting step includes introducing into the examined blood conduit a doppler flow-wire comprising a doppler transducer mounted substantially at its distal end.

7. The method of claim 6 wherein said inserting step includes positioning said doppler transducer at a distal region of the examined blood conduit relative to said site and said moving steps include retracting said doppler flo-wire.

8. The method of claim 7 wherein said retracting of said doppler catheter is performed at a substantially constant rate.

9. The method of claim 6 wherein said doppler type measurement comprises, introducing into said blood conduit a doppler catheter comprising a doppler transducer substantially at its distal end;

moving said doppler transducer to said region;

measuring a velocity of blood flow in said region;

moving said doppler transducer to said zone; and measuring a velocity of blood flow in said zone.

10. The method of claim 9 wherein said cross-sectional area of said region $A_n$ is related to the cross-sectional areas of said zone $A_k$ and said catheter $A_c$ by $$A_n = A_c + (A_k - A_c) \times (V_k/V_n)$$

wherein $V_k$ and $V_n$ are velocities measured in said zone and said examined region respectively.

11. The method of claim 10 wherein said velocity is a phasic velocity.

12. The method of claim 10 wherein said velocity is a mean velocity averaged over at least one heart beat.

13. The method of claim 9 further comprising controlling the orientation of said doppler transducer relative to the measured blood flow to achieve reliable velocity measurements.

14. The method of claim 9 wherein said velocity is a phasic velocity.

15. The method of claim 9 wherein said velocity is a mean velocity averaged over at least one heart beat.

16. The method of claim 9 further comprising:

moving said doppler transducer to a second region of said blood conduit;

measuring a velocity of blood flow in said second region; and determining cross-sectional area of said second region based on said measured velocities.

17. The method of claim 16 further comprising the steps of forming a profile of said blood conduit by correlating said measured cross-sectional areas and their locations.

18. The method of claim 17 further comprising visually displaying said profile.

19. The method of claim 1 further comprising repeating the method of claim 1 at a later date and comparing the velocity measurement provided by the method of claim 1 at an earlier date with that at a later date.

20. A system for detecting a partial occlusion in a blood conduit of a hemodialysis patient comprising:

a velocity detector insertable into different regions of an examined blood conduit at a selected site used for hemodialysis access, said velocity detector constructed to provide velocity signals representative of velocity of the blood flow at said different regions; and a processor constructed to receive said velocity signals from said detector and arranged to compare said velocity signals measured at different regions of the examined blood conduit to create a velocity profile.

21. The system of claim 20 wherein said velocity detector is a doppler type detector.

22. The system of claim 21 wherein said doppler type detector includes a doppler catheter comprising a proximal end and a distal end;

a doppler transducer mounted substantially at said distal end of said catheter; and a doppler velocimeter connectable to said proximal end of said catheter.

23. The system of claim 21 wherein said doppler type detector includes a doppler flo-wire comprising a proximal end and a distal end;

a doppler transducer mounted substantially at said distal end of said flo-wire; and a doppler velocimeter connectable to said proximal end of said flo-wire.

24. A method of detecting an occlusion in a blood conduit of a hemodialysis patient including, inserting a velocity sensing device into said conduit to provide a velocity signal representative of the velocity of blood flow in said conduit at the location of said device in said conduit and a position signal representative of said location, moving said velocity sensing device through said conduit, and sensing a significant change in said velocity signal and the position signal when said significant change occurs to provide an indication of the location of an occlusion in said blood conduit.

25. A method of detecting an occlusion in a blood conduit of a hemodialysis patient in accordance with claim 24 and further including, inserting a dialysis needle into a blood vessel of said patient, and inserting said velocity sensing device into said conduit through said dialysis needle.

26. Apparatus for detecting an occlusion in a blood conduit of a hemodialysis patient comprising, a velocity sensing device in said conduit constructed and arranged to provide a velocity signal representative of the velocity of blood flow in said conduit at the location of said device in said conduit and a position signal representative of said location, said velocity sensing device being movable through said conduit, and a detector constructed and arranged to sense a significant change in said velocity signal and the position signal when said significant change occurs to provide an indication of the location of an occlusion in said blood conduit.

27. Apparatus for detecting an occlusion in a blood conduit of a hemodialysis patient in accordance with claim 26 and further comprising, a dialysis needle in a blood vessel of said patient, and a flexible lead connected to said velocity sensing device through said dialysis needle constructed and arranged to allow positioning of said device in said conduit from outside said patient.

28. A method of detecting an occlusion in a blood conduit of a hemodialysis patient comprising the steps of:

locating a section of blood flow conduit having a zone of a known cross-sectional area;

substantially all blood passing through said zone also flowing in the examined blood conduit;

measuring a velocity of the blood flow in said zone;

measuring a velocity of the blood flow in a region of the examined blood conduit; and determining a cross-sectional area of said region based on said velocities.

29. The method of claim 28 wherein said measuring velocity includes making a doppler type measurement.

30. The method of claim 29 wherein said doppler type measurement comprises introducing into said blood conduit a doppler transducer located substantially at the distal end of a flo-wire;

moving said doppler transducer to said region;

measuring a velocity of blood flow in said region;

moving said doppler transducer to said zone; and measuring a velocity of blood flow in said zone.

31. The method of claim 30 further comprising controlling the orientation of said doppler transducer relative to the measured blood flow to achieve reliable velocity measurements.

32. The method of claim 30 wherein said velocity is a phasic velocity.

33. The method of claim 30 wherein said velocity is a mean velocity averaged over at least one heart beat.

34. The method of claim 30 further comprising:

moving said doppler transducer to a second region of said blood conduit;

measuring a velocity of blood flow in said second region; and determining cross-sectional area of said second region based on said measured velocities.

35. The method of claim 29 wherein said velocity is a phasic velocity.

36. The method of claim 29 wherein said velocity is a mean velocity averaged over at least one heart beat.

37. The method of claim 29 wherein said doppler type measurement is repeated to monitor time dependence of said determined cross-sectional area.

38. The method of claim 29 wherein said blood conduit is a vein receiving blood from a surgically created shunt that bypasses flow directly from an artery to said vein.

39. The method of claim 29 wherein said blood conduit is an artery supplying blood to a surgically created shunt that bypasses flow directly from an artery to said vein.

40. A system for detecting a stenosis in a blood conduit of a hemodialysis patient comprising:

a detector constructed and arranged to provide velocity signals representative of velocity of the blood flow;

a blood flow conduit having a zone of a known cross-sectional area that intercepts substantially all blood flowing in said blood conduit; and a processor constructed and arranged to receive velocity signals from said detector and provide an area signal representative of a cross-sectional area of a region of said blood conduit.

41. The system of claim 40 wherein said detector is a doppler flowmeter.

42. The system of claim 41 wherein said doppler flowmeter is an ultrasonic pulsed doppler flowmeter.

43. The system of claim 40 wherein said blood flow conduit is a part of a shunt constructed and arranged to connect a selected vein and a selected artery.

44. The system of claim 42 wherein said ultrasonic pulsed doppler flowmeter includes a doppler catheter having distal and proximal ends with a doppler transducer substantially at said distal end and a doppler velocimeter connected to said proximal end.

45. The system of claim 40 further comprising a display, connected to said processor to receive said area signal, constructed and arranged to display the area signals for each region of said blood conduit.

* * * * *